United States Patent

Silvestrini et al.

[11] Patent Number: 6,143,010
[45] Date of Patent: Nov. 7, 2000

[54] CORNEAL VACUUM CENTERING DEVICE

[75] Inventors: Thomas A. Silvestrini, Alamo; Robert A. Proudfoot, Santa Clara; John A. Scholl, Danville, all of Calif.

[73] Assignee: Kera Vision Inc., Freemont, Calif.

[21] Appl. No.: 08/896,754

[22] Filed: Jul. 18, 1997

[51] Int. Cl.[7] ............................................. A61F 9/00
[52] U.S. Cl. .................... 606/166; 606/170; 606/172; 606/180
[58] Field of Search .................... 606/166, 170, 606/172, 180

[56] References Cited

U.S. PATENT DOCUMENTS

| D. 370,257 | 5/1996 | Christopher . |
| 2,249,906 | 7/1941 | Longoria . |
| 3,074,407 | 1/1963 | Moon et al. . |
| 4,026,591 | 5/1977 | Cleaveland . |
| 4,061,146 | 12/1977 | Baehr et al. . |
| 4,205,682 | 6/1980 | Crock et al. . |
| 4,319,575 | 3/1982 | Bonte . |
| 4,417,579 | 11/1983 | Soloviev et al. . |
| 4,423,728 | 1/1984 | Lieberman . |
| 4,429,696 | 2/1984 | Hanna . |
| 4,452,235 | 6/1984 | Reynolds . |
| 4,614,187 | 9/1986 | Mulhollan et al. . |
| 4,619,259 | 10/1986 | Graybill et al. . |
| 4,662,370 | 5/1987 | Hoffmann et al. . |
| 4,688,570 | 8/1987 | Kramer et al. . |
| 4,766,896 | 8/1988 | Pao . |
| 4,796,623 | 1/1989 | Krasner et al. . |
| 4,815,463 | 3/1989 | Hanna . |
| 4,941,093 | 7/1990 | Marshall et al. . |
| 4,997,437 | 3/1991 | Grieshaber . |
| 5,011,498 | 4/1991 | Krumeich et al. . |
| 5,021,057 | 6/1991 | Byrne, Jr. . |
| 5,063,942 | 11/1991 | Kilmer et al. . |
| 5,090,955 | 2/1992 | Simon . |
| 5,108,412 | 4/1992 | Krumeich et al. . |
| 5,318,044 | 6/1994 | Kilmer et al. . |
| 5,368,604 | 11/1994 | Kilmer et al. . |
| 5,372,580 | 12/1994 | Simon et al. . |
| 5,395,385 | 3/1995 | Kilmer et al. . |
| 5,403,335 | 4/1995 | Loomas et al. . |
| 5,486,188 | 1/1996 | Smith . |
| 5,496,339 | 3/1996 | Koepnick . |

FOREIGN PATENT DOCUMENTS

| 2811869 | 9/1979 | Germany . |
| 3838253 | 5/1990 | Germany . |
| AU 336 | 10/1991 | United Kingdom .................... 606/166 |
| WO 88/10096 | 12/1988 | WIPO . |
| WO 89/00404 | 1/1989 | WIPO . |
| WO 91/08711 | 6/1991 | WIPO . |
| AU 3309 | 10/1993 | WIPO .................................... 606/166 |
| WO 95/17144 | 6/1995 | WIPO . |

OTHER PUBLICATIONS

English translation of Brazilian Patent Application No. BR 8705060 (Mar. 21, 1989).

D'Hermies et al., "Biocompatibility of a refractive intracorneal PMMA ring" *Fortschr Opthalmol* (1991) 88:790–793.

Hartmann, Chr., et al., "Intrastromale Implantation Eines Justierbaren Kunststoffringes Zur Hornhautrefraktionsänderung", pp. 465–475. An English language translation of the article is attached.

Kriesberg et al., "Intraocular pressure and intrastromal corneal ring" *Refractive & Corneal Surgery* (1991) 7:303–307.

*Primary Examiner*—Michael Buiz
*Assistant Examiner*—Lien Ngo
*Attorney, Agent, or Firm*—Morrison & Foerster

[57] ABSTRACT

This invention is a vacuum centering device which may be used in conjunction with other surgical instruments in opthomological surgery. The device provides an improved interface with the eye by way of features that reduce interference with a patient's eyelids interocular pressure and/or the propensity to rotate. These features may include a flared outer wall portion which may either be curved or straight for a section, providing a low profile vacuum chamber, and/or the use of a non-circular outer sealing region potentially producing a saddle-shaped outer periphery providing for potentially increased vacuum exposure to the eye and a contour resistant to rotation.

32 Claims, 7 Drawing Sheets

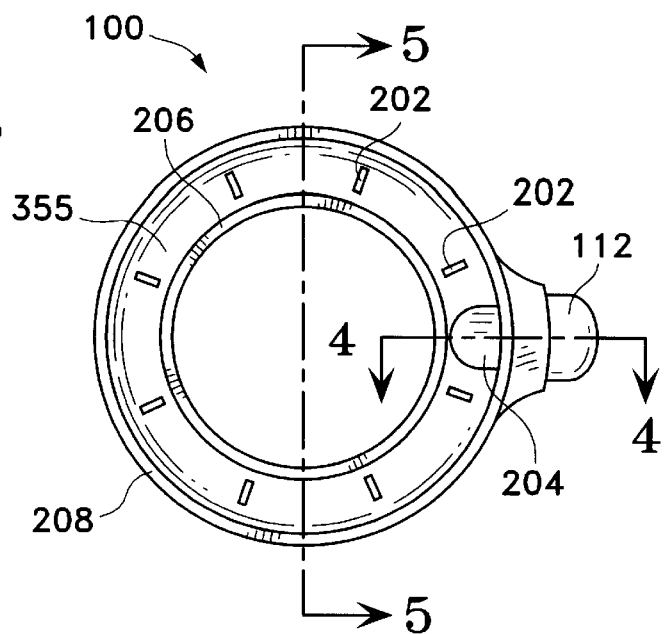
FIG. 3
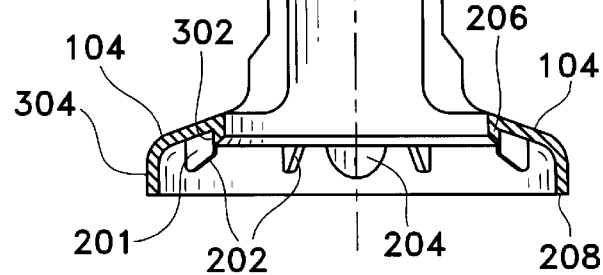
FIG. 4
FIG. 5

CORNEAL VACUUM CENTERING DEVICE

FIELD OF THE INVENTION

The present invention relates generally to corneal surgery and, more particularly, to a vacuum centering device which is fixable in position with respect to the human eye, stabilizing the shape and position of the eye during surgical operations.

BACKGROUND OF THE INVENTION

Anomalies in the overall shape of the eye can cause visual disorders. Hyperopia ("farsightedness") occurs when the front-to-back distance in the eyeball is too small. In such a case, parallel rays originating greater than 20 feet from the eye focus behind the retina. In contrast, when the front-to-back distance of eyeball is too large, myopia ("nearsightedness") occurs and the focus of parallel rays entering the eye occurs in front of the retina. Astigmatism is a condition which occurs when the parallel rays of light do not come to a single point within the eye, but rather have a variable focus due to the fact that the cornea is aspherical and refracts light in a different meridian at different distances. Some degree of astigmatism is normal, but where it is too high, it must often be corrected.

Hyperopia, myopia, and astigmatism are usually corrected by glasses or contact lenses. Surgical methods for the correction of such disorders are known. Such methods include radial keratotomy (see, e.g., U.S. Pat. Nos. 4,815,463 and 4,688,570) and laser corneal Ablation (see, e.g., U.S. Pat. No. 4,941,093). Further methods include the implantation of polymethylmethacrylate (PMMA) rings, allograft corneal tissue, and hydrogels is well documented. U.S. Pat. No. 4,452,235, to Reynolds, for example, describes a method and apparatus for corneal curvature adjustment involving the implantation of polymeric rings in the eye's corneal stroma to change the curvature of the cornea.

Vacuum devices useful for such ocular surgical procedures are common. For instance, U.S. Pat. No. 4,423,728, to Lieberman, shows a cam-guided trephine for selectively cutting a circular or V-shaped groove about the cornea. The device utilizes a pair of suction rings which affix the apparatus onto the sclera of the patients eye. The vacuum is usually less than about 10 cm of water thereby avoiding raising the intraocular pressure above the physiological levels. The suction ring lies in the anatomically constant area just outside the limbus.

Similarly, U.S. Pat. No. 4,997,437 to Grieshaber, shows a process and apparatus for cornea grinding. The device has a base member which is held to the conjunctiva of the eye by a vacuum space formed about the periphery of the cornea. A rotary grinder is attached to the base member and slides onto the eye through the interior bore of the base member.

Also, U.S. Pat. No 4,662,370, to Hoffmann et al., shows an apparatus for performing lamellar refractive cornea surgery. The device has a base adapted for placement on the sclera of the eye with an annular recess forming a vacuum space for holding the device to the eye while pressing the cornea against an insert of a predetermined shape. The applanate surface of the insert dictates the shape of the corneal lamella cut by a knife riding on a support mounted on the base.

Similarly, U.S. Pat. No. 5,496,339, to Korpnick, shows an apparatus for making a shaped cut of the cornea in the correct position in order to make the refractive change desired. The device has a base with a suction ring adapted to be positioned and held against the sclera of the eye with a corrected surface portion of an insert drawn to the cornea of the eye by the vacuum applied. A knife mounted to a drive device cuts corneal tissue only directly underneath the surface portion.

U.S. Pat. No. 5,011,498, to Krumeich et al., shows a cutting apparatus for excision of a round corneal disk. One embodiment of the invention is installed on an eye vacuum ring having an inner surface that is conformed to the outer surface of the eye. A vacuum draws the eye conforming surface to the outer surface of the eye.

U.S. Pat. No. 5,108,412 to Krumeich et al., shows a suction ring for surgical operations on the eye. The ring has an outer right-angle section and an inner annular ring member carried by the outer section. The inner annular ring has a generally right-angle triangular cross-section. The inner ring possesses an eye-conforming surface and a plurality of segments on its two remaining exterior surfaces. This configuration provides a vacuum space between the two exterior surfaces of the inner ring and the interior of the outer right-angle section. A vacuum draws the eye conforming surface to the outer surface of the eye.

None of these publications provide for a rotationally and translationally stable base member having an improved fit with the surrounding tissue of the eye.

U.S. Pat. No. 5,021,057, to Byrne, Jr., shows an instrument to be used during ocular surgery for the rapid closure of the eye to prevent expulsive choroidal hemorrhaging resulting from operative complications. The device is dome-shaped so to form a seal with the eye to stop expulsive flow. It requires a close fit to the curvature of the anterior ocular surface including the limbus of the eye in order to form a seal. The device has an offset opening allowing a doctor to place sutures in the eye. The location of the opening can be changed by rotating the device by its attached handle. No provision is made for a vacuum space, an open region leaving the cornea substantially exposed or for preventing rotation about the eye.

U.S. Pat. No. 5,063,942, U.S. Pat. No. 5,318,044, U.S. Pat. No. 5,368,604 and U.S. Pat. No. 5,395,385, to Kilmer et al., disclose a device and for re-profiling a cornea. The device may rest on a resilient vacuum ring which is adapted to sit on the sclera of the eye and surrounding the cornea which is to be re-profiled. The top side of the vacuum ring has a number of positioning pins which allow it to be connected to the remainder of the profiling apparatus. No provisions are made in these publications for a discrete, substantially stable vacuum interface region or for preventing rotation of the vacuum ring.

U.S. Pat. No. Des. 370,257, to Christopher, shows an ocular solution applicator having a cup shape and a flat, ovaloid footprint. No provisions are made for a vacuum space an interface with the eye, access to the cornea of the eye, a low-profile application of the curved outer surface to accommodate potentially impinging eyelid tissue or a saddle-shaped periphery.

U.S. Pat. No. 4,026,591, to Cleaveland, shows a contact lens handling tool for placing contact lenses upon the eye or alternately removing them. The publication shows a device having an ovalized an outer cup adapted to bottom in the outer peripheral portion of the eye socket of the user, serving to hold the eyelids back so one of a number of cup-shaped attachments that has clearance to deliver or retrieve a contact lens. Each of the inner cups is shaped to create an appropriate interface with contact lenses. The inner cups will not come into contact with a user's eyelids. The outer cup is not configured to fit into the eye. No provisions are made for a vacuum interface with the eye, access to the cornea of the eye or for preventing rotation of the base member.

One optional aspect of the invention is the use of contact surfaces or vanes which engage the front of the eye to prevent rotation of the inventive device during use.

U.S. Pat. No. 4,429,696, to Hanna, shows a surgical apparatus for precisely cutting out the cornea of the eye by making at least one circular incision. The device is held to the front of the eye by a series of claws, which optionally may be retractable, and suction placed on the central portion of the eye during the cutting operation. There is no suggestion of using the claws in cooperation with a vacuum space.

U.S. Pat. No. 4,417,579, to Soloview et al., shows a surgical device for marking out the cornea in ophthalmosurgial operations utilizing a multiplicity of plates so formed to cause elastic non-destructive deformation of the cornea upon application of force. There is no suggestion of using these plates to prevent rotation or to use them in cooperation with a vacuum space.

U.S. Pat No. 5,403,335, to Loomas et al. discloses a surgical apparatus for producing a generally circular, interlamellar pathway within the cornea. The device is comprised of three major components including a vacuum centering guide having an annular vacuum chamber and a multiplicity of vanes to prevent rotation. There is no suggestion of providing the vacuum centering guide with a sloped or flared edge or an ovalized outer boundary allowing for less interference with impinging eyelid tissue.

The invention described herein is an corneal vacuum centering device. It may serve as an independent apparatus or as a suction ring component which detachably adheres to the front of the eye for guiding and precisely positioning surgical instruments relative to the eye.

BRIEF DESCRIPTION OF THE DRAWINGS

FIG. 3 is a bottom view of the vacuum centering device.

FIG. 4 is a partial cross-sectional view of the vacuum centering device looking along the line 4—4 as shown in FIG. 3.

FIG. 5 is a cross-sectional view looking along the line 5—5 as shown in FIG. 3.

SUMMARY OF THE INVENTION

Figure 1:
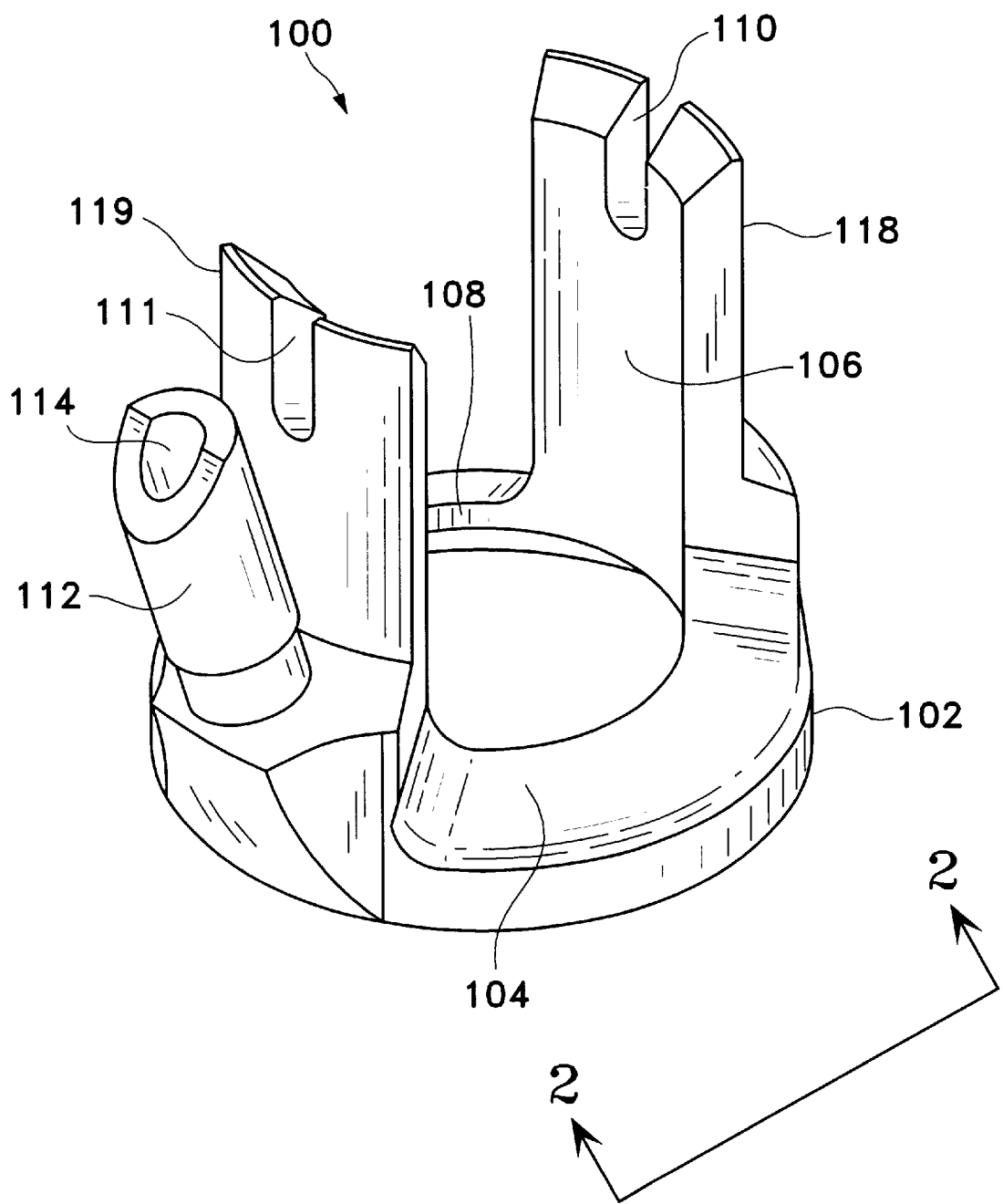
FIG. 1 is a front perspective view of the vacuum centering device according to the principle of the present invention.

The present invention is directed to providing a vacuum centering device exhibiting an improved interface with a patients eye. The construction of this invention includes features that will, either independently or in combination, decrease interference problems with a patient's eyelids, prevent rotation of the base carrying operative instruments and/or decrease intraocular pressure. Interference problems, unwanted rotation and high intraocular pressure may all result in patient discomfort and unnecessary tissue damage. The construction of this invention also includes structure for preferred viewing of the eye and workpieces used in conjunction with the inventive device, additionally providing for reduction of the potential for tissue damage and patient discomfort.

The present invention includes a vacuum chamber formed between an inner wall having a first sealing region for contacting the eye and outer wall extending from said inner wall in a flared manner turning back toward the eye and forming a second sealing region.

This device may be such that the flared section turns back toward the eye over at least one curved section. Such a curved section may have a constant radius of curvature. The radius of curvature may be between about 23 mm and about 26 mm so as to approximate the curvature of the eye and form a wall near parallel to and potentially in close proximity to the eye.

Alternately, the device may be such that the flared section includes a straight section extending from the inner wall at an angle of less than ninety degrees.

The present invention may be such that the inner wall of the device forms a central bore. The central bore need not be cylindrical, it can be otherwise curvilinear or have a faceted surface. Regardless, the bore will have a central axis. In this configuration, the first sealing region may be a substantially annular surface centered about the central axis. Where the inventive device includes such an annular first sealing region, the annular surface may be oriented at an angle relative to the central axis between about 30 degrees to about 60 degrees. More particularly, the angle may be about 45 degrees. In this configuration, the second sealing region may have an ovaloid projection as viewed along the central axis. More particularly, this ovaloid projection may be substantially elliptical. When it is shaped in an elliptical manner this ovaloid projection will result in a saddle-shape upon the substantially spherical shape of the eye.

The present invention may include a plurality of eye contacting surfaces positioned within the vacuum chamber. These surfaces, adapted to contact the eye and thereby help prevent rotation of the device when under vacuum, may be vane-like or otherwise shaped. Further, these vanes or surfaces may be oriented radially from the central axis. These surfaces or vanes may number between 6 and 32.

The present invention may also include a guide member having one guiding surface aligned with the central axis, a pair of such surfaces or more. The guide member may include at least one open-end slot. The guiding surface or surfaces may be cylindrical. Where the invention utilizes two vertically-oriented cylindrical surfaces, they may subtend an arc angle between about 15 degrees and about 150 degrees. More particularly, they subtend arc angles between about 20 and 45 degrees.

Alternately, the present invention may comprise a main body having both a proximal and distal end, a central axis therebetween, and a sealing chamber at the distal end with the sealing chamber having an inner sealing region of contacting the eye and a non-circular outer sealing region for contacting the eye and a wall running between these regions. The sealing chamber may have a port for supplying a vacuum source.

The outer sealing region may have an ovaloid projection as viewed along the central axis. More particularly, the sealing region may have an elliptical projection when viewed along the central axis. Also, the inner sealing region may have an annular surface concentric with the central axis.

Further the present invention may have a plurality of contact surfaces position within the chamber adapted to contact the eye. These surfaces, as above, may be vane-shape or fashioned otherwise. The surfaces may be oriented radially from the central axis. The number of surfaces in this variation of the invention where the outer sealing region is non-circular may be between about 15 and about 45. More particularly, the number of contact surfaces may be between about 25 and about 35.

The present invention as understood more directly above may further include a guide member having at least one guide surface aligned with the central axis. This guide member may include at least one cylindrical guide surface subtending an arc angle of less than about 270 degrees. Alternatively, the guide member may include two cylindrical surface each subtending an arc angle of between about 15 degrees and about 150 degrees.

DESCRIPTION OF THE INVENTION

Referring to the drawings in detail wherein like numerals indicate like elements, the present invention generally involves a vacuum centering device for use in performing surgical operations on the eye. The vacuum centering device is useful for accurately and consistently aligning or guiding surgical tools to a desired position on or in the eye or through a desired motion relative to the eye. The present invention generally involves a sealing chamber, to which vacuum pressure is applied to fixedly couple the centering device to the eye, and a guide member for accurately directing a surgical tool to a desired location on the eye.

The vacuum centering device is useful with a wide variety of surgical tools and methods. Once securely fixed in position by the application of vacuum pressure, the centering device allows the surgeon to use any number of devices in succession and still maintain registration with a desired position on the eye. For example, the present invention may be constructed to provide sufficient guiding surfaces for use with various scalpels or incisors, corneal markers, corneal dissectors and other such instruments which require accurate placement relative to the eye. Specific examples of such instruments and procedures can be found in U.S. Pat. No. 5,403,335 to Loomas et al., the entirety of which is herein incorporated by reference; and co-pending U.S. application Ser. No. 08/796,555 titled "Improved Device and Method for Inserting a Biocompatible Material Into the Cornea of the Stroma" and filed on Feb. 7, 1997, the entirety of which is herein incorporated by reference.

The present invention involves a vacuum centering device constructed to provide a sealing chamber with a low profile, flared exterior surface for improved fit within the immediate vicinity of the eye. The low profile exterior surface may have a variety of constructions including radiused or straight chamfered.

The vacuum centering device of the present invention may also be constructed to provide guide surfaces constructed to precisely manipulate the desired surgical instrument and yet to provide greatly improved visual and instrument access during surgical operations. Although the invention will be described with reference to guiding surgical instruments having generally cylindrical bodies it should be understood that the present invention can be used in conjunction with other instruments and devices having of varied constructions.

The present invention also involves a sealing chamber that provides for lower interocular pressures and superior resistance to translational slip caused by torsional and lateral loads encountered during certain surgical procedures. The sealing chamber generally defines a vacuum space between an inner and outer wall which seals against the eye upon application of vacuum pressure. The outer wall of the sealing chamber may be generally circular or may be ovaloid or elliptical.

Figure 2:
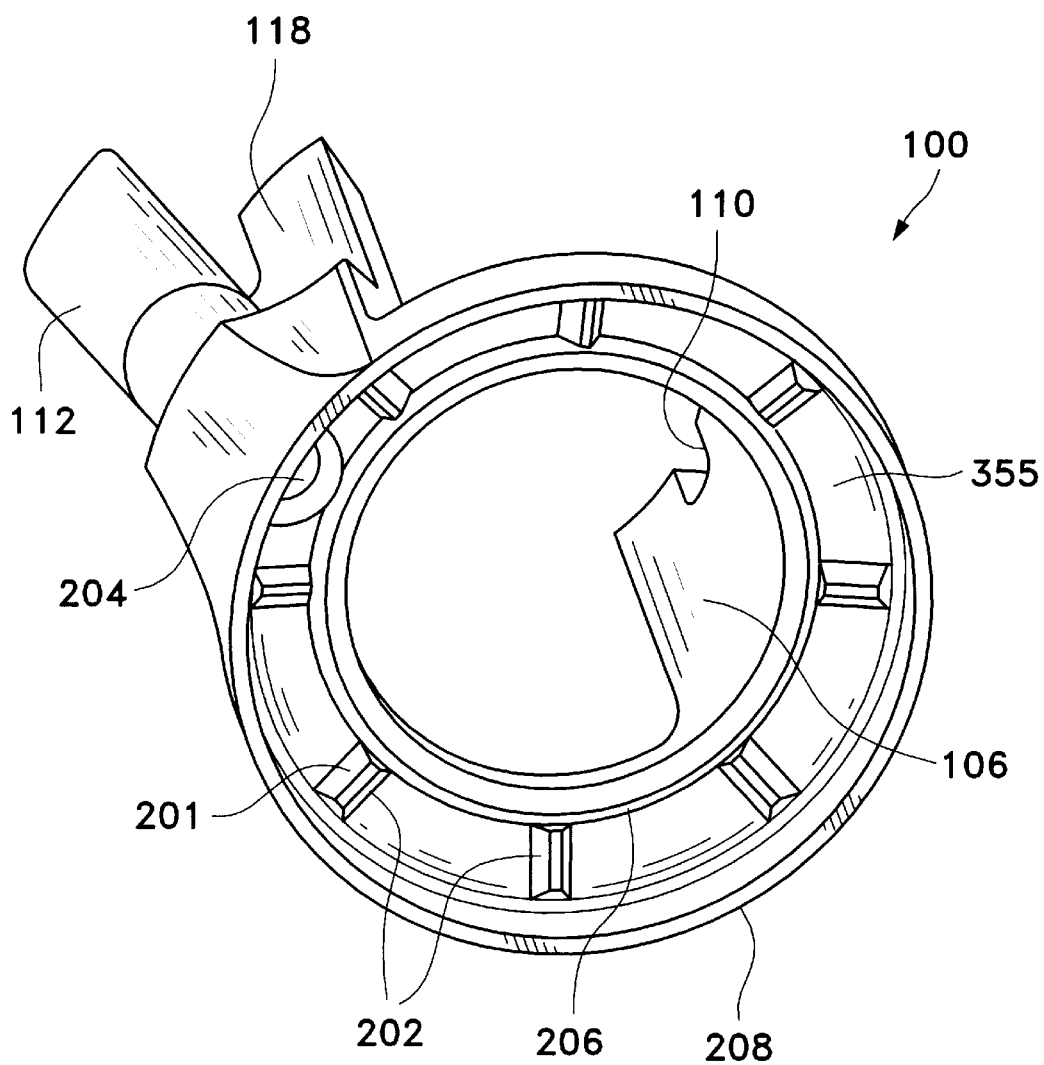
FIG. 2 is a perspective view of the vacuum centering device looking approximately along the line 2—2 as shown in FIG. 1.

The vacuum centering device generally includes a main base portion which includes a sealing chamber and at least one guide support member. Top and Bottom perspective views of a vacuum centering device (100) according to the principles of the present invention are shown in FIGS. 1 and 2. The vacuum centering device (100) has a base (102). In a preferred embodiment, guide support members (118, 119) extend substantially vertically from the base (102) and are positioned opposite one another. The base (102) includes a sealing chamber or vacuum space (355) to which vacuum pressure may be applied by way of tubular connection (112) which has an interior lumen (114) in fluid communication with vacuum port (204) inside the vacuum space (355).

The guide support members (118, 119) have guide features or surfaces for receiving and accurately positioning a surgical instrument which is to be used. Such guide surfaces may have any suitable shape to mate with said instrument. In the preferred embodiment shown in FIGS. 1 through 8, guide support members (118, 119) have a cylindrical guide surface (106) for receiving and mating cylindrical instruments.

Mating cylinders are particularly useful when a mating surgical instrument is required to be rotated relative to the vacuum centering device (100) about the central axis (210, see FIGS. 4 and 5) during a surgical procedure. Such rotation is commonly required, for example, when forming intrastromal channels using circular dissectors. The cylindrical guide surfaces (106) provide free rotation of a mating cylindrical instrument within the vacuum centering device (100) and yet have sufficient height to prevent unacceptable angular movement of the surgical instrument.

If relative rotation of the surgical instrument and the vacuum centering device (100) is not desired, one or both of the guide support members (118, 119) may optionally be constructed with a feature that engages the surgical instrument to prevent rotation. In a preferred embodiment, guide support members (118, 119) have open-ended slots (110, 111). The open-ended slots (110, 111) engage one or more pins or protrusions (not shown) on a mating surgical instrument to prevent rotation of the surgical instrument about the central axis (210). Open-ended slots (110, 111) may also be use to key or lock a surgical instrument into one or more rotational positions relative to the vacuum centering device (100). In the preferred embodiment of FIG. 1, a surgical instrument having a mating pin or protrusion would have two fixed positions that exactly 180 degrees apart.

The maximum angular movement or a surgical instrument allowed by the guide surfaces (106) is a function of the clearance between the mating surfaces of the surgical instrument and the guide surfaces (106), the height of the guide surfaces (106), and the total subtended angle of the guide surfaces (106). To improve both visual access and instrument access by the surgeon, guide surfaces (106) subtend less than 360° around the base (102). Preferably, each guide support member (118, 119) and associated guide surface (106) subtend an arc angle of between about 15° to about 360°. Most preferably, the subtended arc angle for each guide support member (118, 119) and associated guide surfaces (106) will be between about 20° and 45°. As seen in the FIG. 1, this arrangement leaves adequate open area between the guide support members to allow the surgeon to view the eye during surgery as well as access the eye with any necessary surgical instrument.

As mentioned above, the base (102) has a sealed chamber or vacuum space (355). Referring to FIGS. 2 through 6, the vacuum space (355) is generally bounded by an inner wall (302) and an outer wall (304). The inner wall may form a second cylindrical guide surface (108) to assist guide surfaces (106) in controlling the position of a surgical instrument.

An important aspect of the vacuum centering device (100) is the shape of the outer wall (304). Outer wall (304) is constructed to have a reduced profile surface (104) which provides for an improved fit of the base (102) between the upper and lower eyelids. The surface (104) may be sloped, tapered, flared, chamfered, radiused, or otherwise shaped to provide a lower profile above the surface of the eye. The reduced profile allows the vacuum centering device (100) to be fixed to the eye with much less severe retraction of the surrounding eyelids. This in turn provides increased stability of the vacuum centering device as well as increased patient comfort.

The number of radial vanes (201) may be positioned within the vacuum space to provide contact surfaces (202) for contacting the eye. These contact surfaces are employed to engage the surface of the eye to provide resistance to rotation of the vacuum centering guide (100) against torsional loading, for instance from a rotating surgical instrument. The radial vanes (201) and associated contact surfaces (202) also serve to prevent the surface of the eye to be pulled in too far within the vacuum space upon application of vacuum pressure. Because the low profile outer wall may be in close proximity to the surface of the eye, a number of radial vanes (201) may be positioned as shown to prevent the eye from being drawn into the vacuum space to such an extent that it substantially impairs or even completely blocks the vacuum space (355).

Figure 6:
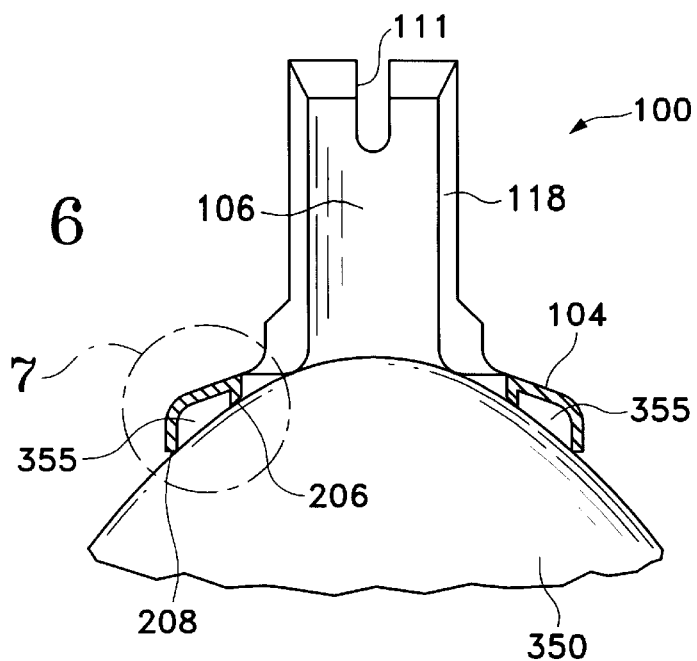
FIG. 6 is a cross-sectional view of the vacuum centering device as placed upon the eye.

Referring now to FIG. 6, the vacuum centering device (100) is shown in positioned on the surface of a mammalian eye (350). The sealed chamber or vacuum space (355) is completed as first sealing region (206) associated with inner wall (302) and second sealing region (208) associated with outer wall (304) engage the surface of eye (350).

Figure 7:
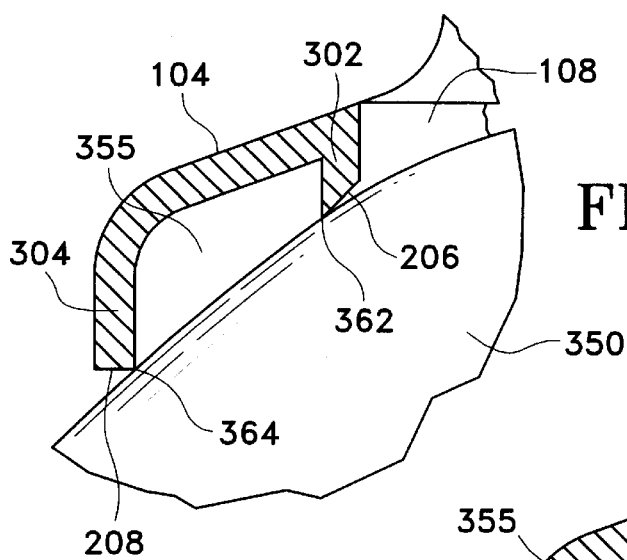
FIG. 7 is a detailed view of section 7—7 as shown in FIG. 6 depicting the vacuum centering device placed upon the eye while the device is not under vacuum.
Figure 8:
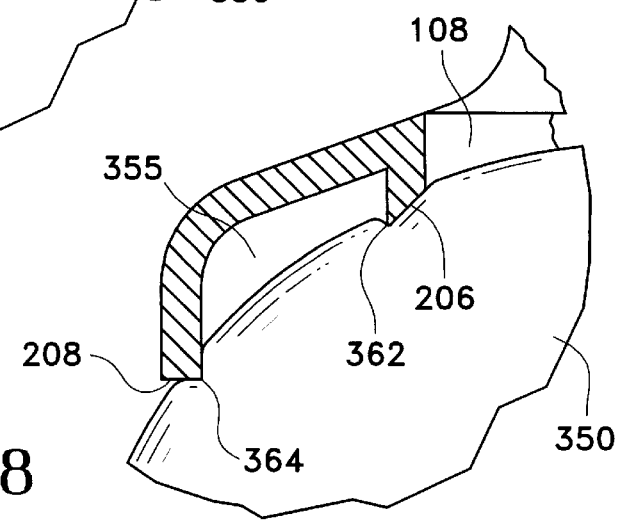
FIG. 8 is a detailed view of section 7—7 as shown in FIG. 6 depicting the vacuum centering device placed upon the eye while the device is under vacuum.

FIG. 7 is a magnified view of a portion of the vacuum space (355) positioned against the surface of the eye (350). FIG. 7 shows more clearly the preferred details of the first sealing region (206) and second sealing region (208) before the application of vacuum pressure to the vacuum space (355). Both the first and second sealing regions (206, 208) are preferably surfaces that tend to contact the surface of the eye on an edge. First sealing region (206) is approximately at an angle of between 25° and 65°, preferably 45°, with the central axis (210) and contacts the eye (350) at first edge (362). Second sealing region (208) is preferably at about 90° to said central axis (210) and contacts the surface of the eye (350) at second edge (364).

As vacuum pressure is applied to the vacuum space (355) the first edge (362) and the second edge (364) begin to deform and dig into the surface of the eye (350). This initial edge contact of the first and second sealing regions (206, 208) greatly improves the ability of the vacuum centering device to seal against the eye (350). In that way, a lower overall pressure may be applied to effectuate proper sealing, and therefore, a lower interocular pressure will result during surgery. To obtain the proper sealing functions outline above, the inner and outer walls are preferably made of relatively stiff materials. Preferably the vacuum centering device is made from stainless steel or titanium, but many plastics and synthetic or natural rubbers having a hardness above Shore A 90° have been found to be sufficient.

Another preferred aspect of the present invention is illustrated with respect to FIGS. 9 through 12 and involves a construction having a non-circular outer wall. As will be discussed below, a non-circular outer wall provides a larger contact area with the surface of the eye which in turn facilitates the use of lower applied pressures. In addition, a non-circular wall has a projected contact path around the generally spherical eye that yields improved resistance to translational and rotational slippage.

Figure 9:
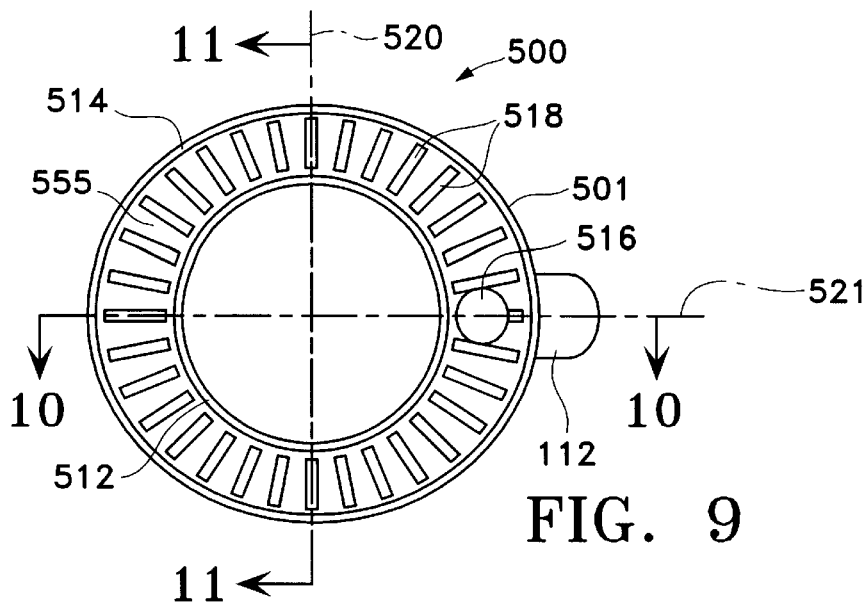
FIG. 9 is a bottom view of the vacuum centering device having a saddle-shaped base showing the outer periphery having an ovaloid projection.
Figure 10:
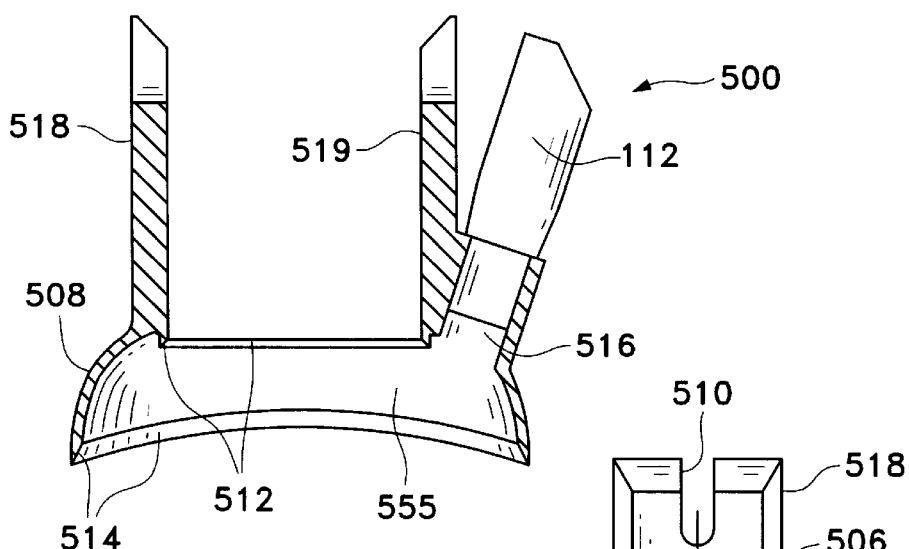
FIG. 10 is a cross-sectional view of the vacuum centering device having a saddle-shaped base looking along the line 10—10 as shown in FIG. 9.
Figure 11:
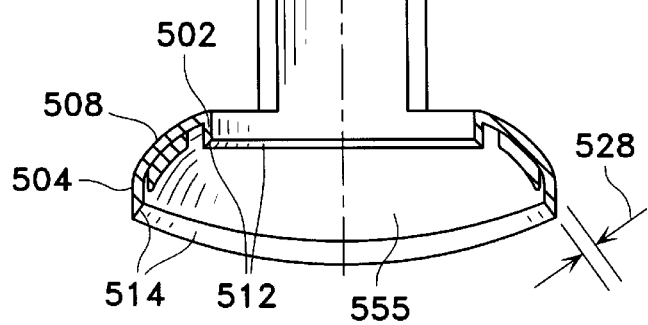
FIG. 11 is a cross-sectional side view of the vacuum centering device having a saddle shaped base looking along the line 11—11 as shown in FIG. 9.

As shown in FIG. 9, the vacuum centering device (500) has a base (501) which has generally vertical guide support members (518, 519) having guide surfaces (506) and optional open ended slots (510) in the manner described above. Inner wall (502) and outer wall (504) form vacuum space (555). Outer wall (504) has a low-profile exterior surface (508) adapted in close proximity to the surface of the eye (not shown) as described above with reference to FIGS. 1 through 8. The depth (528) of the vacuum space (555) may range from 0.200 inches to 0.010 inches and is typically in the range of about 0.020 inches to about 0.100 inches.

Inner wall (502) has a first sealing region (512) and outer wall has a second sealing region (514). The vacuum space (555) is completed as the sealing regions, are caused to seal against the surface of the eye upon the application of a vacuum pressure through vacuum port (516) by way of connecting tube (112). As described above, the first and second sealing regions (512, 514) are constructed to engage the eye at their respective edges before the application of vacuum pressure.

An important aspect of this embodiment is that the outer wall (504) is non-circular. In a preferred embodiment, the profile of the second sealing region (514) associated with the outer wall (504) is ovaloid as viewed from the central axis (570). Most preferably, the sealing region has a profile that is elliptical as shown in FIG. 9, having a major axis (521) and a minor axis (520).

Figure 12:
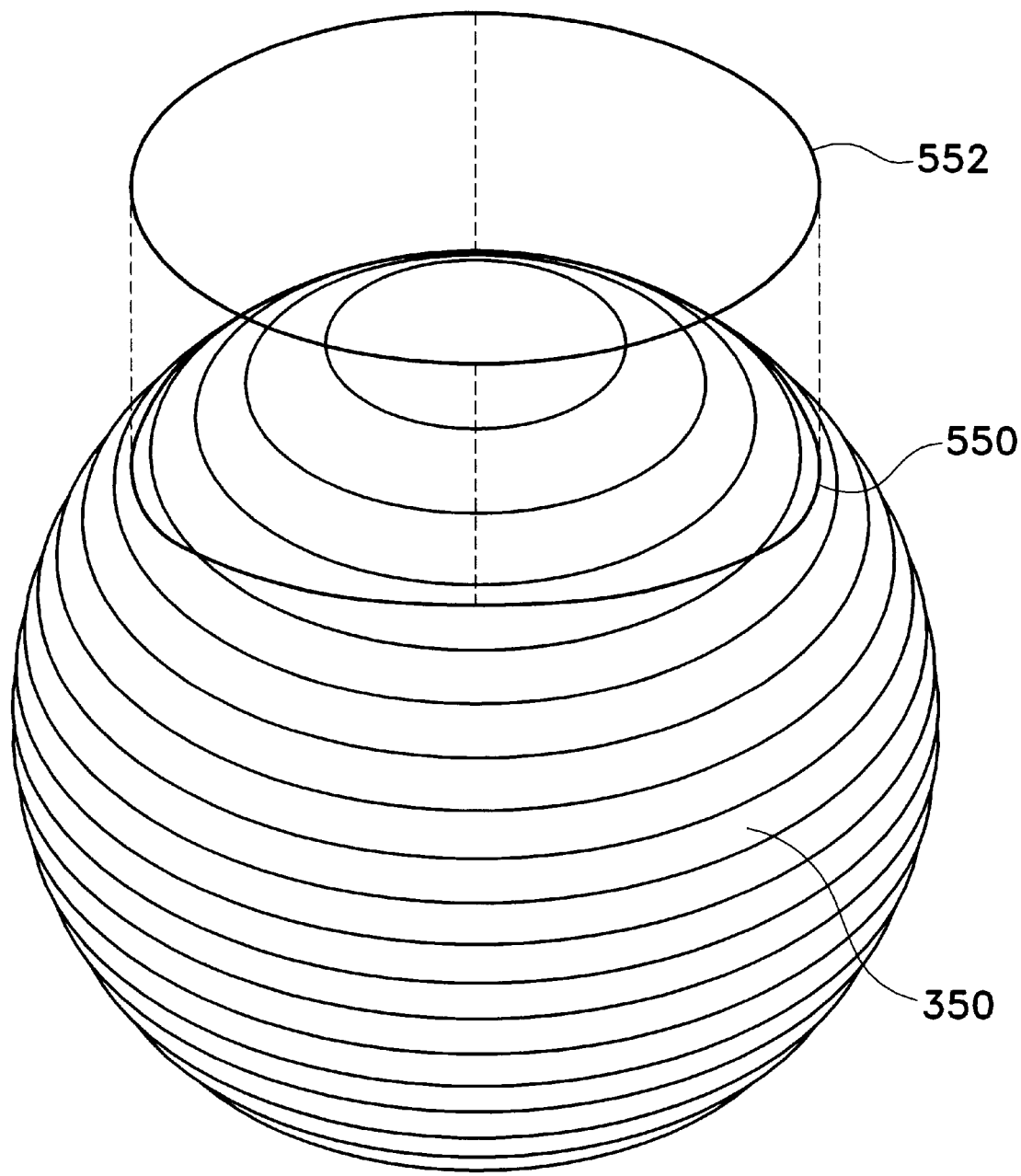
FIG. 12 is a projection of an oval onto a sphere, representing an eye, this projection indicating the saddle shape of the invention as shown in FIG. 8.

Referring to FIG. 12, the elliptical shape (552) of the outer wall (504) and the second sealing region (514) results in a complex "saddle-shape" (550) when projected onto the spherical shape of the eye.

The shape (550) taken by the second sealing region (514) is more effective in many respects. First, it provides a better fit to a patient's eye as it interferes less with a patient's eye lids. The ovaloid shape more closely resembles the shape of an open eye. Second, this shape (550) of the second sealing region (514) advantageously resists torsional loading and improves translations stability over plain circular designs. Additionally, the ovaloid shape can be maximized to provide greater coverage of the eye than a similar device utilizing a circular profile. This provides greater area for the vacuum to pull on, thereby increasing the force with which the device is held in place; also, it provides space for larger or more vanes adapted to prevent rotation.

Alternately, the ovaloid shape can be used to minimize the height of the device lessening the need to retract tissue to accommodate it. The decrease in overall height and subsequent loss of vacuum area that would be lost for a circular device can be recovered with the extending the outer wall around the eye in the direction of major axis (521), thereby adding vacuum area. The preferred embodiment of the present invention makes a compromise between lessening the required height of the device to help aid the critical advantage offered by the sloped aspect of the outer wall and maximizing the area for the vacuum to pull on.

The preferred variant of the vacuum space (555) again contains a number of vanes which serve to help prevent rotation of the support base during the ophthalmic operation. Increasing the number of vanes also reduces interocular pressure as the vacuum force over the eye is distributed over a larger area of the increased number vanes. Additionally, the use of a greater number of vanes allow the use of a lower vacuum to hold the device to the eye. The pressure range acceptable for use with the vacuum centering device described herein in the range of 0–30 inches Hg.

Figure 13:
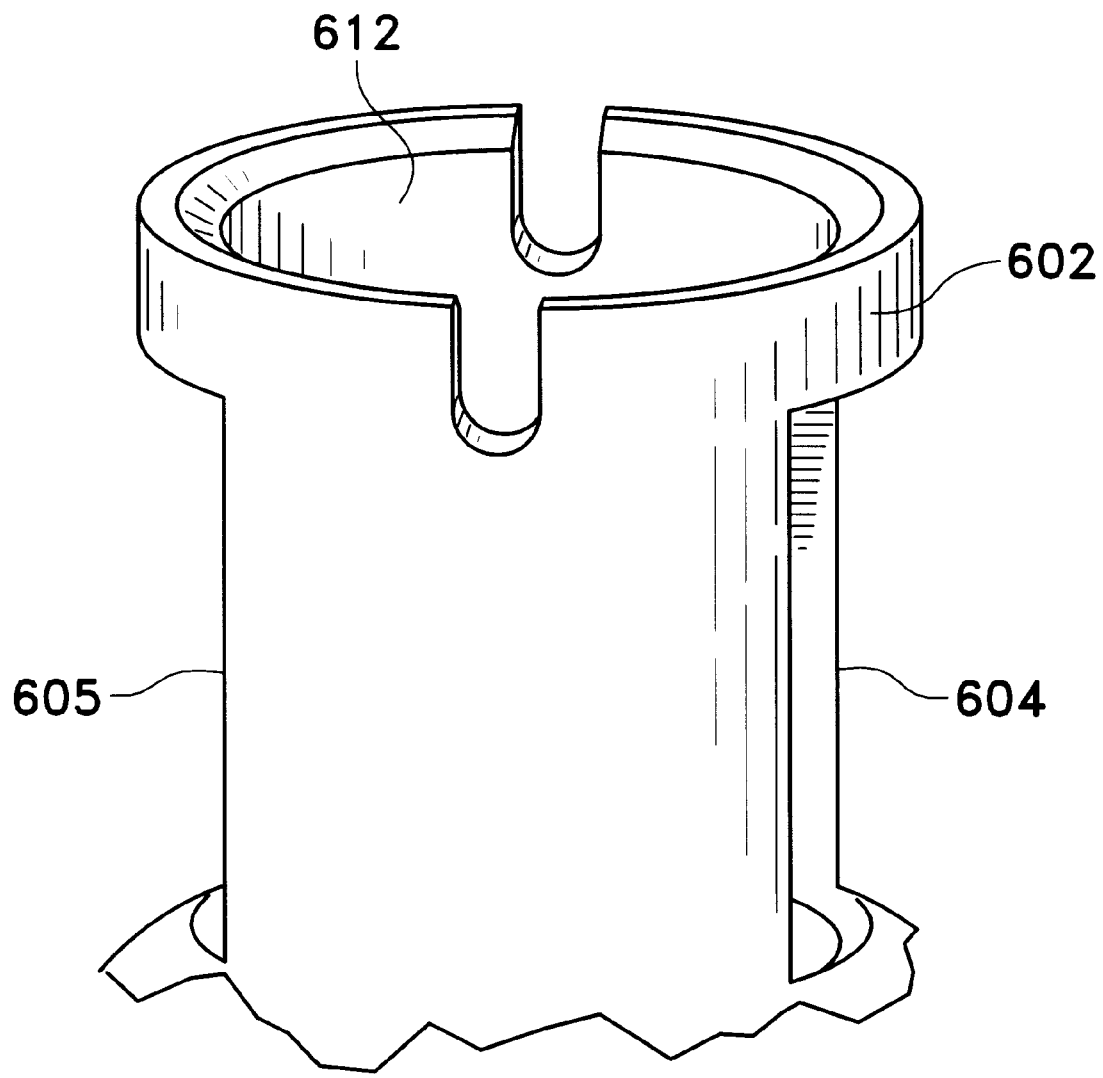
FIG. 13 is an alternate embodiment of the guide members.

FIG. 13 shows an alternate embodiment for the guide support members that provide guide surfaces (612) for the surgical instruments. In this embodiment, the vacuum centering device has a generally cylindrical bore having a top ring (602) and access windows (604, 605) for visual and instrument access. The top ring may be provided with anti-rotation open-ended slots as shown.

This invention has been described and exemplified in some detail. Those having ordinary skill in this art would recognize variations and equivalents which would be well within the scope of the invention disclosed here but perhaps outside the scope of the appended claims. It is applicants intention that these equivalent variations be included within the scope of this invention.

We claim:

1. A corneal vacuum centering device comprising:

an inner wall having a first sealing region for contacting an eye; and an outer wall having a second sealing for contacting the eye, said outer wall extending outwardly from said inner wall such that said that said inner wall and said outer wall form a sealed chamber when said first and second sealing regions contact eye, said outer wall having an exterior surface, at least a portion of said exterior surface having a flared profile adapted to fit at least partially beneath eyelid tissue when the device is on the eye.

2. The corneal vacuum centering device of claim 1, wherein said flared profile comprises at least one curved section.

3. The corneal vacuum centering device of claim 1, wherein said flared profile comprises at least one substantially straight section positioned at an angle of less than ninety degrees to said inner wall.

4. The corneal vacuum centering device of claim 2 wherein said curved section has a constant radius of curvature.

5. The corneal vacuum centering device of claim 4 wherein said radius of curvature is between about 23 mm and 26 mm.

6. The corneal vacuum centering device of claim 1 wherein said inner wall forms a central bore having a central axis.

7. The corneal vacuum centering device of claim 6 further comprising a plurality of contact surfaces positioned within said chamber, said contact surfaces adapted to contact the eye.

8. The corneal vacuum centering device of claim 7 wherein said contact surfaces are oriented radially from said central axis.

9. The corneal vacuum centering device of claim 8 wherein the number of said contact surfaces is between 6 and 32.

10. The corneal vacuum centering device of claim 6 wherein said first sealing region is substantially an annular surface centered about said central axis.

11. The corneal vacuum centering device of claim 10 wherein said first annular surface is oriented at angle relative to said central axis, said angle being between about 30 degrees to about 60 degrees.

12. The corneal vacuum centering device of claim 11 wherein said angle is about 45 degrees.

13. The corneal vacuum centering device of claim 6 wherein said second sealing region has an ovaloid projection as viewed along the central axis.

14. The corneal vacuum centering device of claim 13 wherein said ovaloid projection is substantially elliptical.

15. The corneal vacuum centering device of claim 6 further comprising a guide member having at least one guide surface aligned with said central axis.

16. The corneal vacuum centering device of claim 15 wherein said guide surface is a cylindrical surface.

17. The corneal vacuum centering device of claim 15 wherein said guide member comprises two vertically oriented cylindrical surfaces.

18. The corneal vacuum centering device of claim 17 wherein each of said cylindrical surfaces subtend an arc angle of between about 15 degrees and about 150 degrees.

19. The corneal vacuum centering device of claim 18 wherein each of said cylindrical surfaces subtend an arc angle of between about 20 degrees and about 45 degrees.

20. The corneal vacuum centering device of claim 15 wherein said guide member further includes at least one open-ended slot.

21. A corneal vacuum centering device comprising:

a main body member having a proximal end, a distal end, a central axis, and a sealing chamber located at said distal end;

said sealing chamber having an inner sealing region for contacting the eye, a non-circular outer sealing region when viewed along said central axis for contacting the eye, and a contiguous wall therebetween.

22. The corneal vacuum centering device of claim 21 wherein said outer sealing region has an ovaloid projection when viewed along said central axis.

23. The corneal vacuum centering device of claim 21 wherein said outer sealing region has an elliptical projection when viewed along said central axis.

24. The corneal vacuum centering device of claim 21 wherein said inner sealing region is an annular surface concentric with said central axis.

25. The corneal vacuum centering device of claim 21 wherein said sealing chamber further comprises a port for supplying vacuum pressure.

26. The corneal vacuum centering device of claim 21 further comprising a plurality of contact surfaces positioned within said chamber, said contact surfaces adapted to contact the eye.

27. The corneal vacuum centering device of claim 26 wherein said contact surfaces are oriented radially from said central axis.

28. The corneal vacuum centering device of claim 27 wherein the number of said contact surfaces are between about 15 and about 45.

29. The corneal vacuum centering device of claim 28 wherein the number of said contact surfaces are between about 25 to 35.

30. The corneal vacuum centering device of claim 21 further comprising a guide member having at least one guide surface aligned with said central axis.

31. The corneal vacuum centering device of claim 30 wherein said guide member comprises at least one cylindrical surface subtending an arc angle of less than about 270 degrees.

32. The corneal vacuum centering device of claim 30 wherein said guide member comprises two cylindrical surfaces each subtending an arc angle of between about 15 degrees and about 150 degrees.

* * * * *